United States Patent
Kroll et al.

(10) Patent No.: US 7,369,898 B1
(45) Date of Patent: May 6, 2008

(54) SYSTEM AND METHOD FOR RESPONDING TO PULSED GRADIENT MAGNETIC FIELDS USING AN IMPLANTABLE MEDICAL DEVICE

(75) Inventors: Mark W. Kroll, Simi Valley, CA (US); Gene A. Bornzin, Simi Valley, CA (US); Sergio Shkurovich, Encino, CA (US); Nirav Dalal, North Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 505 days.

(21) Appl. No.: 11/020,438

(22) Filed: Dec. 22, 2004

(51) Int. Cl.
   *A61N 1/08* (2006.01)
   *A61B 5/05* (2006.01)
(52) U.S. Cl. ........................ 607/63; 600/411
(58) Field of Classification Search ................ 600/410, 600/411; 607/30, 27, 63
   See application file for complete search history.

(56) References Cited

U.S. PATENT DOCUMENTS

| | | | | |
|---|---|---|---|---|
| 4,746,864 | A | | 5/1988 | Satoh .......................... 324/309 |
| 4,772,812 | A | * | 9/1988 | Desmarais .................... 326/88 |
| 5,063,348 | A | | 11/1991 | Kuhara et al. .............. 324/307 |
| 5,142,229 | A | | 8/1992 | Marsden ...................... 324/248 |
| 5,438,990 | A | * | 8/1995 | Wahlstrand et al. ........ 324/260 |
| 5,629,622 | A | * | 5/1997 | Scampini ..................... 324/247 |
| 5,644,230 | A | | 7/1997 | Pant et al. ................... 324/247 |
| 5,662,694 | A | * | 9/1997 | Lidman et al. ............... 607/60 |
| 5,697,958 | A | * | 12/1997 | Paul et al. .................... 607/31 |
| 5,722,998 | A | * | 3/1998 | Prutchi et al. ................ 607/30 |
| 5,814,085 | A | | 9/1998 | Hill ............................. 607/14 |
| 5,817,136 | A | * | 10/1998 | Nappholz et al. ............. 607/17 |
| 6,052,614 | A | * | 4/2000 | Morris et al. ................ 600/509 |
| 6,067,472 | A | * | 5/2000 | Vonk et al. ................... 607/28 |
| 6,101,417 | A | * | 8/2000 | Vogel et al. .................. 607/30 |
| 6,188,926 | B1 | * | 2/2001 | Vock .............................. 607/9 |
| 6,725,092 | B2 | * | 4/2004 | MacDonald et al. ........... 607/2 |
| 6,795,730 | B2 | * | 9/2004 | Connelly et al. ............... 607/9 |
| 6,795,736 | B2 | * | 9/2004 | Connelly et al. ............. 607/36 |
| 6,925,328 | B2 | * | 8/2005 | Foster et al. ................... 607/9 |
| 6,937,906 | B2 | * | 8/2005 | Terry et al. ................... 607/63 |
| 6,963,779 | B1 | * | 11/2005 | Shankar ....................... 607/30 |
| 7,015,393 | B2 | * | 3/2006 | Weiner et al. ................ 174/36 |
| 7,050,855 | B2 | * | 5/2006 | Zeijlemaker et al. ......... 607/27 |

(Continued)

FOREIGN PATENT DOCUMENTS

WO    WO 03/037429 A1    5/2003

*Primary Examiner*—Eric Winakur
*Assistant Examiner*—Helene Bor

(57) ABSTRACT

Implantable medical devices, such as pacemakers or implantable cardioverter defibrillators (ICDs), are vulnerable to the powerful magnetic fields associated with magnetic resonance imaging (MRI). In particular, pulsed gradient components, if strong enough, can induce parasitic currents that may damage the device or cause parasitic pacing that may trigger an arrhythmia in the patient. The static magnetic field components of the MRI typically do not induce parasitic currents, even though they may be as strong as the pulsed gradient components. Accordingly, techniques are described herein for specifically addressing the pulsed gradient components of the MRI fields so as to reduce the risk of parasitic currents. In one example, a pacemaker switches to tri-state pacing outputs in the presence of strong pulsed gradient magnetic fields. The device continues with normal bi-state pacing outputs so long as the pulsed gradient fields are not strong, even in the presence of a strong static magnetic field. As an added safety feature, the pacemaker switches to fixed-rate ventricular pacing whenever strong static MRI fields are detected.

15 Claims, 6 Drawing Sheets

U.S. PATENT DOCUMENTS

| | | | |
|---|---|---|---|
| 7,076,283 B2 * | 7/2006 | Cho et al. | 600/410 |
| 7,082,328 B2 * | 7/2006 | Funke | 607/9 |
| 7,164,950 B2 * | 1/2007 | Kroll et al. | 607/36 |
| 7,183,768 B2 * | 2/2007 | Min | 324/260 |
| 7,231,251 B2 * | 6/2007 | Yonce et al. | 607/27 |
| 2002/0116033 A1 * | 8/2002 | Greatbatch et al. | 607/33 |
| 2003/0082570 A1 * | 5/2003 | Cho et al. | 600/410 |
| 2003/0083570 A1 | 5/2003 | Cho et al. | 600/410 |
| 2003/0144704 A1 * | 7/2003 | Terry et al. | 607/27 |
| 2003/0144705 A1 | 7/2003 | Funke | 607/27 |
| 2003/0144706 A1 | 7/2003 | Funke | 607/30 |
| 2004/0088012 A1 * | 5/2004 | Kroll et al. | 607/9 |
| 2004/0199069 A1 * | 10/2004 | Connelly et al. | 600/412 |
| 2004/0251042 A1 * | 12/2004 | Weiner et al. | 174/36 |
| 2005/0043761 A1 * | 2/2005 | Connelly et al. | 607/2 |
| 2005/0113669 A1 * | 5/2005 | Helfer et al. | 600/412 |
| 2005/0113676 A1 * | 5/2005 | Weiner et al. | 600/421 |
| 2005/0113873 A1 * | 5/2005 | Weiner et al. | 607/2 |
| 2005/0113874 A1 * | 5/2005 | Connelly et al. | 607/2 |
| 2005/0113876 A1 * | 5/2005 | Weiner et al. | 607/36 |
| 2005/0197677 A1 * | 9/2005 | Stevenson | 607/36 |

* cited by examiner

SYSTEM AND METHOD FOR RESPONDING TO PULSED GRADIENT MAGNETIC FIELDS USING AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for protecting implantable medical devices from fields associated with magnetic resonance imaging (MRI).

BACKGROUND

MRI is an effective, non-invasive technique for generating sharp images of the internal anatomy of the human body, which provides an efficient means for diagnosing disorders such as neurological and cardiac abnormalities and for spotting tumors and the like. Briefly, the patient is placed within the center of a large superconducting magnet that generates a powerful static magnetic field. The static magnetic field causes protons within tissues of the body to align with an axis of the static field. A pulsed radio-frequency (RF) magnetic field is then applied causing the protons to begin to process around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

A significant problem with MRI is that its strong magnetic fields can interfere with the operation of any medical devices, particularly pacemakers or ICDs, implanted within the patient. Typically, pacemakers and ICDs include pulse generators for generating electrical pacing pulses and shocking circuits for generating stronger defibrillation shocks. A set of conductive leads connect the pulse generators and shocking circuits to electrodes implanted within the heart. An individual pacing pulse is applied by using the pulse generators to generate a voltage difference between a pair of the electrodes, typically between a tip electrode implanted within the right ventricle and the pacemaker housing or "can." A defibrillation shock is applied by using the shocking circuits to generate a much larger voltage difference between a pair of the electrodes, typically between a coil electrode implanted within the right ventricle and the pacemaker housing. The pulse generators, shocking circuits, leads and electrodes, as well as the tissue and fluids between the electrodes, collectively provide a conduction loop. During normal pacing operation of the device, current is permitted to flow around the conduction loop. The precise normal loop is from the pacing output circuitry through the pacing lead conductor to the lead tip, then into the right ventricular muscle, and then into the chest skeletal muscles and then back to the can and thence to the inner circuitry again. Care must be taken to ensure that defibrillation shocks do not induce currents within the pacing conduction loops, which might damage the pacing circuitry. This includes internal as well as external defibrillation shocks. Diodes and the like are used to prevent such damage.

State of the art pacemakers and ICDs exploit lead systems having numerous electrodes, thus presenting numerous possible conduction paths. Accordingly, diodes are provided along all vulnerable current pathways. Under normal operating conditions, these safeguards are helpful. However, the powerful magnetic fields of an MRI system can abuse these protection components and induce currents to flow around the pacing current paths by generating unwanted voltage differentials between various electrode pairs. The resulting currents and voltages can have severe consequences to the patient. In particular, the pulsed gradient components of the MRI can include currents among the conduction paths sufficient to trigger unwanted pulses or shocks. These are referred to as parasitic currents. The resulting rapid pulses could, in certain cases, induce life-threatening fibrillation of the heart. The RF fields are not a problem as such fields do not stimulate cardiac cells and are blocked by bypass capacitors in the pacemaker or ICD and hence do not enter the device.

Another significant concern is that the induced voltages are sensed by the pacemaker as heartbeats. In most pacing modes, such as VVI or DDI, the pacemaker then assumes that the heart needs no help and will then block its pacing output (i.e. delivery of a pacing pulse is inhibited.) This could cause a "pacing dependent" patient to pass out or die. VVI and DDI are standard device codes that identify the mode of operation of the device. Others standard modes include DDD, VDD and VOO. Briefly, DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. VOO identifies fixed-rate ventricular pacing, which ignores any potentially sensed cardiac signals. This mode is quite different from the aforementioned "demand" modes, which only pace when the pacemaker determines that the heart is "demanding" pacing. Numerous other device modes of operation are possible, each represented by standard abbreviations of this type.

Various methods have been proposed to address the effects of interference by MRI systems on implantable medical devices. Typically, such safeguard techniques operate to detect the strong fields associated with an MRI and then switch sensing modes or pacing modes in response thereto. See, for example, U.S. Patent Application 2003/0083570 to Cho et al.; U.S. Patent Application 2003/0144704 to Terry et al.; U.S. Patent Application 2003/0144705 to Funke; U.S. Patent Application 2003/0144706 also to Funke and U.S. Pat. No. 6,795,730 to Connelly, et al., entitled "MRI-Resistant Implantable Device."

Heretofore, however, it does not appear that the typical techniques for safeguarding implantable medical devices from MRI fields properly distinguish among the different types of magnetic fields generated during MRI. Typical techniques merely monitor for a strong magnetic field and, if one is detected, safeguard procedures are then initiated by the implanted device. However, the effects on the patient and on the implanted device can vary depending upon the particular field being applied. One technique that at least addresses the distinction among the different types of MRI fields is set forth in U.S. Patent Application 2004/0088012 of Kroll et al., entitled "Implantable Stimulation Device With Isolating System For Minimizing Magnetic Induction," which is incorporated by reference herein. Techniques are described therein that employ separate magnetic field sensors and RF signal sensors. In one example, safeguard procedures are activated only if both sensors detect strong fields, thus reducing risks of false MRI detection. In other examples, safeguard procedures are activated if either a strong magnetic field or a strong RF signal is detected. However, room for improvement remains. In particular, the aforementioned technique of Kroll et al. does not distinguish between static magnetic fields and pulsating gradient magnetic fields. The static magnetic field of an MRI system typically does not induce parasitic currents, whereas the pulsating gradient components can induce such currents. Accordingly, it would be highly desirable to provide improved MRI safeguarding techniques that distinguish between static magnetic fields and pulsating gradient magnetic fields and it is to this end that the invention is generally directed.

SUMMARY

In accordance with certain illustrative embodiments, techniques are provided for use by an implantable medical device for responding to strong magnetic fields, such as those generated during MRI. Briefly, the device monitors for magnetic fields and evaluates the strength of pulsed gradient components, if any, of the magnetic fields. The device then controls its functions based on the strength of the pulsed gradient components, if any, so as to reduce the risk of abnormal functionality caused by the strong pulsed gradient magnetic fields.

In one example, wherein the device is a pacemaker or ICD and the fields are MRI fields, the device first detects the MRI system by sensing for any magnetic field, static or otherwise, that exceeds a predetermined MRI detection threshold, which is set based on the magnetic field strengths expected to be encountered during a typical MRI. If MRI fields are sensed, the device then determines whether there is a strong static component. If so, the device switches to the VOO pacing mode to prevent the device from erroneously inhibiting pacing pulses in response to induced currents mistakenly identified as intrinsic heartbeats. Then, the device determines whether there are any pulsating gradient components and, if so, whether the gradients are strong enough to present a significant risk of parasitic currents. If a strong pulsed gradient field is detected, the device tri-states electrical outputs to its leads to prevent any parasitic currents from arising, i.e. the outputs are caused to switch among positive, negative and open circuit values rather than between just positive and negative values as in normal pacing. If a pulsed gradient field is detected but is relatively weak, normal pacing connections (i.e. bi-state connections) are used. In other words, in that case, normal pacing connections are used despite the presence of the large static magnetic field of the MRI and despite the presence of pulsating magnetic field components because the gradient of the pulsating components is not large enough to present a significant risk of parasitic currents.

The invention is perhaps most advantageously implemented in pacemakers and ICDs for responding to MRI fields but principles of the invention may be exploited within other implantable medical devices for responding to other strong magnetic fields as well.

BRIEF DESCRIPTION OF THE DRAWING

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI-Responsive System

Figure 1:
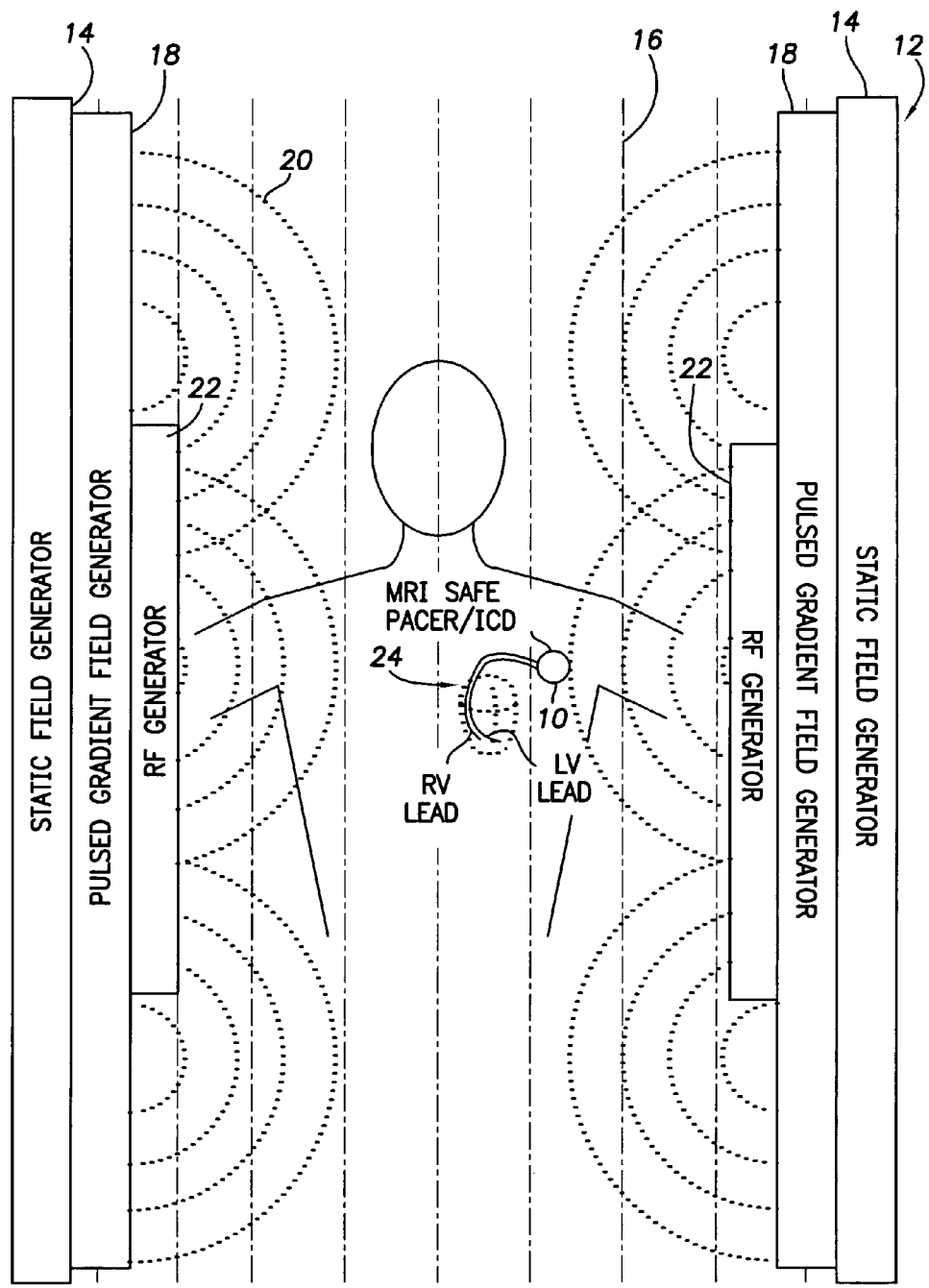
FIG. 1 is a stylized representation of an MRI system along with a patient with an MRI-responsive pacer/ICD implanted therein that is capable of sensing pulsed gradient MRI fields and adjusting its operation to prevent any significant risk of parasitic currents induced by strong pulsed gradient fields.
Figure 4:
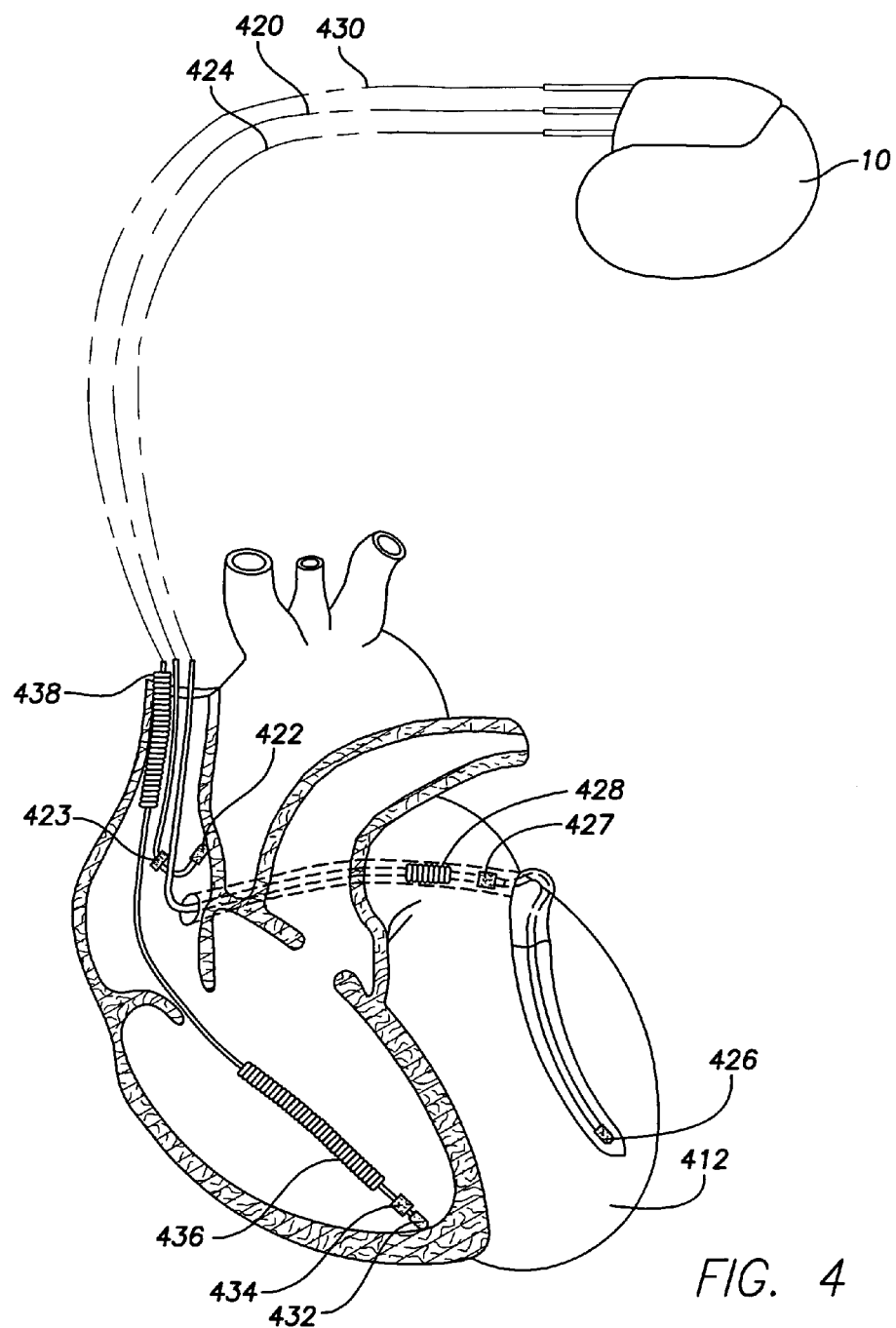
FIG. 4 is a simplified, partly cutaway view, illustrating the pacer/ICD of FIG. 1 along with a full set of leads implanted in the heart of the patient.

FIG. 1 illustrates an implantable MRI-responsive pacer/ICD 10 that incorporates internal components for detecting and responding to the presence of fields generated by an MRI system 12. The MRI system includes a static field generator 14 for generating a static magnetic field 16 and a pulsed gradient field generator 18 for selectively generating pulsed gradient magnetic fields 20. The MRI system also includes an RF generator 22 for generating pulsed RF magnetic fields. The RF fields are not shown in FIG. 1 so as not to obscure the other fields, which are more pertinent to the invention. Other components of the MRI, such as its sensing and imaging components are not shown either. MRI systems and imaging techniques are well known and will not be described in detail herein. For exemplary MRI systems see, for example, U.S. Pat. No. 5,063,348 to Kuhara, et al., entitled "Magnetic Resonance Imaging System" and U.S. Pat. No. 4,746,864 to Satoh, entitled "Magnetic Resonance Imaging System." A lead system 24 is coupled to the pacer/ICD for sensing electrical cardiac signals and for delivering pacing and cardioversion therapy. In FIG. 1, only two leads are shown, a right ventricular (RV) lead and a left ventricular (LV) lead. A more complete lead system is illustrated in FIG. 4, discussed below. Note that the fields shown in FIG. 1 are stylized representations of magnetic fields intended merely to distinguish between static and pulsed gradient fields. Actual MRI fields generally have far more complex patterns.

Figure 2:
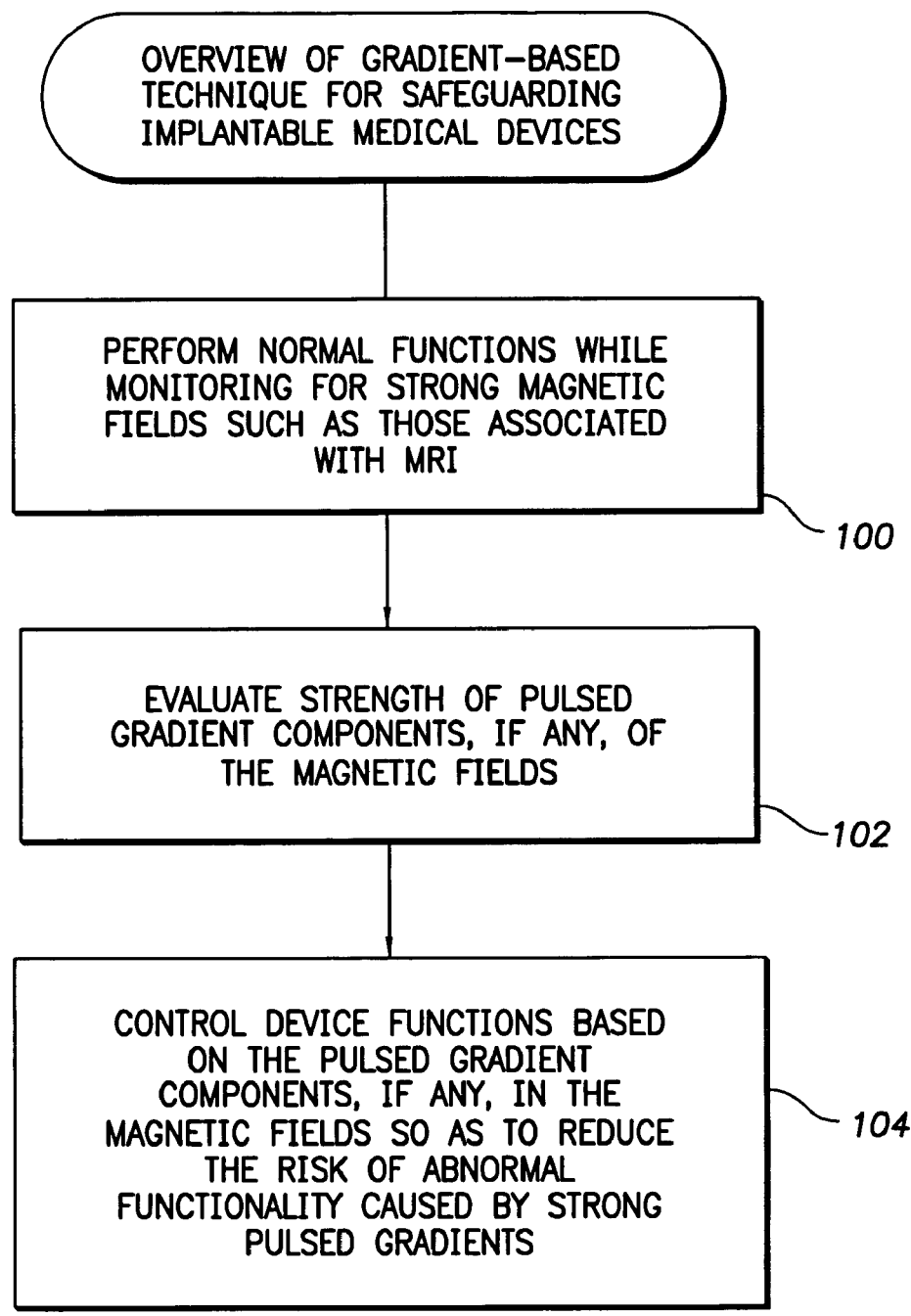
FIG. 2 is a flow diagram providing an overview of MRI responsive techniques performed by the pacer/ICD of FIG. 1.

FIG. 2 provides a high-level overview of the MRI-responsive techniques performed by the pacer/ICD of FIG. 1 or other implantable medical device. At step 100, the device performs normal functions while monitoring for any strong magnetic fields, such as those associated with MRI. By "normal" functions, it is meant that the implanted device performs functions in a manner that does not specifically take into account the presence of strong magnetic fields. For a pacer/ICD, normal functions involve any of a variety of cardiac rhythm management functions, such as anti-bradycardia pacing, anti-tachycardia pacing (ATP), overdrive pacing, and the like, that involve delivering electrical stimulation to heart tissue using otherwise conventional techniques. For other implanted devices, such as neural stimulators, normal functions may involve the delivery of electrical stimulation to nerves or other tissues, again in a manner that that does not specifically take into account the presence of strong magnetic fields. In any case, at step 102, the device evaluates the strength of pulsed gradient components, if any, of the magnetic fields. Then, at step 104, the device controls its functions based on the strength of the pulsed gradient components of the magnetic fields so as to reduce the risk of abnormal functionality caused by strong pulsed gradients.

In an example described in more detail below, where the device is a pacer/ICD capable of tri-state pacing, the device switches to tri-state pacing from otherwise conventional bi-state pacing if the pulsed gradient is so strong that there is a risk of parasitic pacing. These are just some examples of how a pacer/ICD may be equipped to respond to the pulsed gradient components of an MRI field or other strong magnetic field. Other techniques may alternatively be employed for use with other implantable devices, consistent with the functionality of those devices and with the general principles of the invention.

Thus, FIG. 2 provides an overview of techniques wherein an implantable medical device specifically accounts for pulsed gradient components of strong magnetic fields, which are a principal cause of abnormal functionality arising due to MRI, particularly within pacer/ICD systems. This permits the implanted device to properly respond to any strong pulsed gradients so as to reduce the risk of abnormal functionality that may arise due to strong pulsed gradients.

The following provides a detailed description of an exemplary technique specifically for use with a pacer/ICD in the presence of an MRI.

Exemplary Threshold-Based MRI-Responsive Technique

Figure 3:
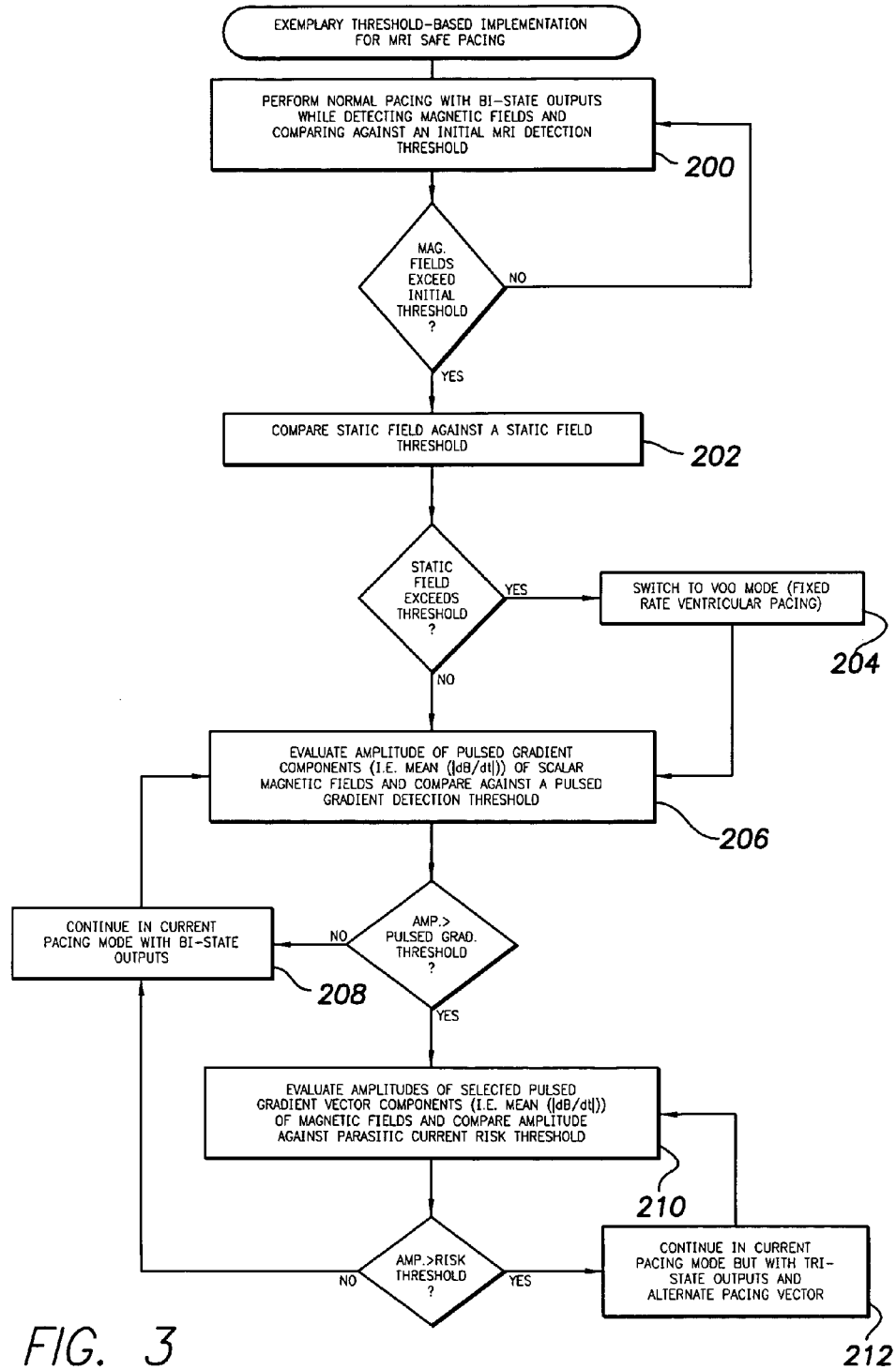
FIG. 3 is a flow diagram providing a more detailed illustration of a particular, exemplary MRI responsive technique performed by the pacer/ICD of FIG. 1.

FIG. 3 illustrates an exemplary MRI-responsive technique performed by the pacer/ICD of FIG. 1. At step 200, the device performs normal pacing functions while detecting and measuring magnetic fields using a magnetometer, which may be mounted within the housing of the pacer/ICD or external thereto. Exemplary magnetometers or other magnetic field sensors for use with pacer/ICDs are discussed in the above-referenced patent application to Kroll et al. Also at step 200, the pacer/ICD compares the strength of the magnetic fields against a predetermined initial MRI detection threshold, representative of typical minimal magnetic field strengths expected to be encountered by a patient during an MRI. An exemplary initial threshold value is 0.2 tesla. Step 200 is primarily performed to detect the presence of an MRI system by detecting the strong static magnetic field applied during MRI. However, any sufficiently strong magnetic field, static or otherwise, is detected at step 200.

As already explained, by "normal" pacing, it is meant that cardiac rhythm management functions are performed which do not specifically take into account the presence of strong magnetic fields. Depending upon the capabilities of the device, the normal pacing of the device may include sophisticated ATP techniques, overdrive pacing techniques, or the like. In addition, the pacer/ICD may be configured to perform Automatic Mode Switching (AMS) wherein the pacemaker reverts from a tracking mode such as a VDD or DDD mode to a nontracking mode such as VVI or DDI mode. Normal pacing is also performed using otherwise conventional bi-state pacing circuitry.

In any case, so long as strong magnetic fields are not detected at step 200, normal pacing continues. However, if strong magnetic fields are detected indicative of an MRI or other magnetic system, the pacer/ICD then, at step 202, compares the static component of the magnetic fields against a static field threshold. If the static field exceeds the static field threshold, the device automatically switches to the VOO mode, at step 204. This is to address the risk that voltages induced by the static MRI fields might be misinterpreted by the pacemaker as intrinsic heartbeats. In most modes, such as VVI or DDI, if intrinsic heartbeats are detected, the pacemaker then assumes that the heart needs no pacing pulses and will then block or inhibit its pacing output. This could cause a "pacing dependent" patient to pass out or even die.

Then, at step 206, the device evaluates whether the magnetic fields include pulsed gradient components (such as field 20 of FIG. 1) associated with MRI. More specifically, at step 206, the magnetometer is employed to: (1) detect dB/dt, i.e. the time derivative of the scalar magnetic field B; (2) evaluate the mean of |dB/dt|; and compare it against pulsed gradient detection threshold indicative of the minimum gradient expected for MRI systems. A suitable pulsed gradient detection threshold is 10 tesla/second. Step 206 is primarily performed to detect the pulsed gradient components of MRI. However, any sufficiently strong pulsed gradient magnetic field, MRI or otherwise, is detected at step 206.

If the mean of |dB/dt| does not exceed the pulsed gradient detection threshold, then pacing continues at step 208 in the current pacing mode with bi-state outputs. The current pacing mode of step 208 will be the VOO mode, if step 204 was performed due to a strong static field. Otherwise, the current pacing mode will be the normal mode initially performed at step 200. However, if the mean of |dB/dt| exceeds the pulsed gradient detection threshold of step 206, step 210 is then performed wherein the pacer/ICD evaluates vector components of the pulsed gradient field to determine if tri-state pacing is instead necessary. In particular, the pacer/ICD determines whether the strength and orientation of the pulsed gradient is such that it presents a significant risk of parasitic pacing or other abnormal functionality. More specifically, at step 210, the magnetometer is employed to: (1) detect $dB_i/dt$, i.e. the time derivative of the vector magnetic field B along one (or more) selected axes "i" of particular concern; (2) evaluate the mean of $|dB_i/dt|$; and compare it against a parasitic current risk threshold indicative of a risk of parasitic currents. A suitable parasitic current risk threshold is 15 tesla/second. A particular axis of concern is the axis perpendicular to the plane of the front of the chest. To be more precise, the most sensitive axis is the axis perpendicular to the plane that best passes through the pacemaker lead as it winds around from the pacemaker to the RV tip. A strong pulsed magnetic field gradient along this axis presents a significant risk of parasitic currents begin induced.

If the mean of $|dB_i/dt|$ for any axis of concern "i" exceeds the risk threshold, the device tri-states its pacing outputs at step 212, i.e. pacing continues in the current pacing mode but with tri-state outputs. The device tri-states the pacing output while the pulsed gradient is large along any axis of concern so as to prevent parasitic currents from being induced that could possibly induce ventricular fibrillation or other arrhythmias. Note that even when the pacemaker is not delivering a pacing pulse, the defibrillation shock protection circuitry provides a complete loop, allowing currents to be induced by the MRI gradient field. By tri-stating the pacing outputs, the current path is thereby opened and parasitic currents along that loop are prevented. Details of tri-state pacing are discussed below in connection with FIG. 6. As noted, pacing at step 212 is performed in the current pacing mode, which may be DDD, VVI, etc, depending upon the mode initially employed at step 200 and whether that mode was switched to VOO at step 204. Hence, so long as the static field is not too strong, the pacer/ICD can continue to safely pace in a sophisticated pacing mode such as DDD, despite the presence of strong pulsed gradient fields, by switching to tri-state outputs. So long as the mean of $|dB_i/dt|$ for each "i" remains below the risk threshold of step 210, pacing in the current pacing mode continues at step 208, with bi-state outputs.

Thus, whereas step 206 is performed to evaluate the amplitude of the gradient of the scalar magnetic field for comparison against an initial pulsed gradient threshold, step 210 is instead performed to evaluate the amplitude of the gradient of the selected components of the magnetic vector field for comparisons against the risk threshold. This is because parasitic currents are only a concern if the amplitude of the gradient of the pulsed magnetic field is large along particular orientations vulnerable to inducing parasitic currents. Accordingly, the device is preferably configured so as to determine the particular component of the vector magnetic field B perpendicular to any current path deemed to be vulnerable to parasitic currents and then to compare that value against a threshold indicative of whether parasitic pacing might be triggered along that path. Tri-state pacing is then activated if that particular component of the magnetic field exceeds the threshold. Preferably, the directional component of the magnetic field is determined by using a vector magnetometer capable of evaluating the gradient of the magnetic field along three perpendicular directions. Based on the three gradient values, the pacer/ICD then uses otherwise conventional vector mathematics to determine the component of the magnetic field along any particular direction. Vector magnetometers are discussed in: U.S. Pat. No. 5,644,230 to Pant, et al., entitled "Miniature Magnetometer And Flexible Circuit" and in U.S. Pat. No. 5,142,229 to Marsden, entitled "Thin-Film Three-Axis Magnetometer And Squid Detectors For Use Therein."

Given that a typical pacing system includes a number of potential parasitic current pathways, it may be desirable to specifically take into account a number of vulnerable directions or axes "i". Accordingly, the device may be programmed to evaluate the component of the gradient field along each of a set of predetermined vulnerable axes. A separate risk threshold value may be provided for use at step 210 for each vulnerable axis based on the circuit characters of potential current loops perpendicular to those axes. Those of ordinary skill in the art may determine the appropriate risk threshold values for use with different potential parasitic current pathways using otherwise conventional techniques. Preferably, however, rather than specifying a plurality of different risk thresholds, a single risk threshold is used, defined with respect to the most vulnerable pathway, which, as noted, is the plane passing through the pacemaker lead as it winds around from the pacemaker to the RV tip. This provides for a simpler implementation. Note, also, that the device need not be programmed to first evaluate the scalar components of the pulsed gradient magnetic field at step 206 before evaluating the vector components of the pulsed gradient magnetic field at step 210. Step 206 is provided to so that the device need not evaluate the vector components, unless necessary, thus conserving processing resources. Alternatively, the device could simply be configured to compare the gradient of the scalar magnetic field against a single risk threshold and tri-stating the outputs accordingly, thus eliminating the vector component analysis entirely. This will likely result in the device switching to tri-state pacing even in situations where not actually required, but provides a still simpler implementation. As can be appreciated, a wide variety of implementations may be provided consistent with the principles of the invention and no attempt is made herein to described or enumerate them all.

In the preferred embodiment, during tri-state pacing at step 212, the device also changes the pacing pulse delivery "vector", i.e. the pair of electrodes used to deliver the pulse. Recall that typically pacing pulses are delivered from RV tip to the can. However, the gradient field, depending upon its orientation, can potentially add or subtract from the voltage of the pacing pulse. For example, 4 volts can be added/subtracted to/from a typical 8 volt pacing pulse. When the gradient field subtracts from the paced voltage, then the result is a 4 V pacing pulse, which may not be sufficient to evoke capture. If the gradient field adds to the voltage of the pacing pulse, then the pulse is 12 volts, which is typically painful or irritating. However, if the pacing pulse is instead delivered between RV tip and RV ring then the addition and subtraction can be significantly reduced or eliminated. Hence, at step 212, the device preferably switches to a different pair of electrodes for delivering pacing pulses so as to maintain, to the extent possible, the optimal pacing pulse voltage. In one example, the device designates a single alternate pair of electrode for delivering pacing pulses (such as RV tip-RV ring) and automatically switches to that alternate pair whenever tri-sate pacing is performed. Alternatively, the device may be programmed to select the best alternate pair of electrodes based on the magnitude and orientation of the gradient magnetic fields so as to best maintain the desired pacing pulse voltage. In still another alternative technique, the device continues to pace RV tip to can, but instead adjusts the voltage generated by the pacing pulse generate in an attempt to compensate for the presence of the gradient field. Note however that, insofar as VOO pacing is concerned, a large fixed voltage, such as 8 volts, is preferred as the sensing for auto-capture typically cannot be trusted in the presence of MRI interference. Again, a wide variety of implementations may be provided consistent with the principles of the invention and no attempt is made herein to describe or enumerate them all.

Although not specifically show in FIG. 3, processing eventually returns to step 200 once magnetic field strength falls below the initial MRI detection threshold, indicating that the MRI system has been turned off. For the sake of completeness, a detailed description of the pacer/ICD of FIG. 1 will now be provided. The general techniques of the invention, however, may be performed using any suitable implantable medical devices.

Exemplary Pacer/ICD

Figure 5:
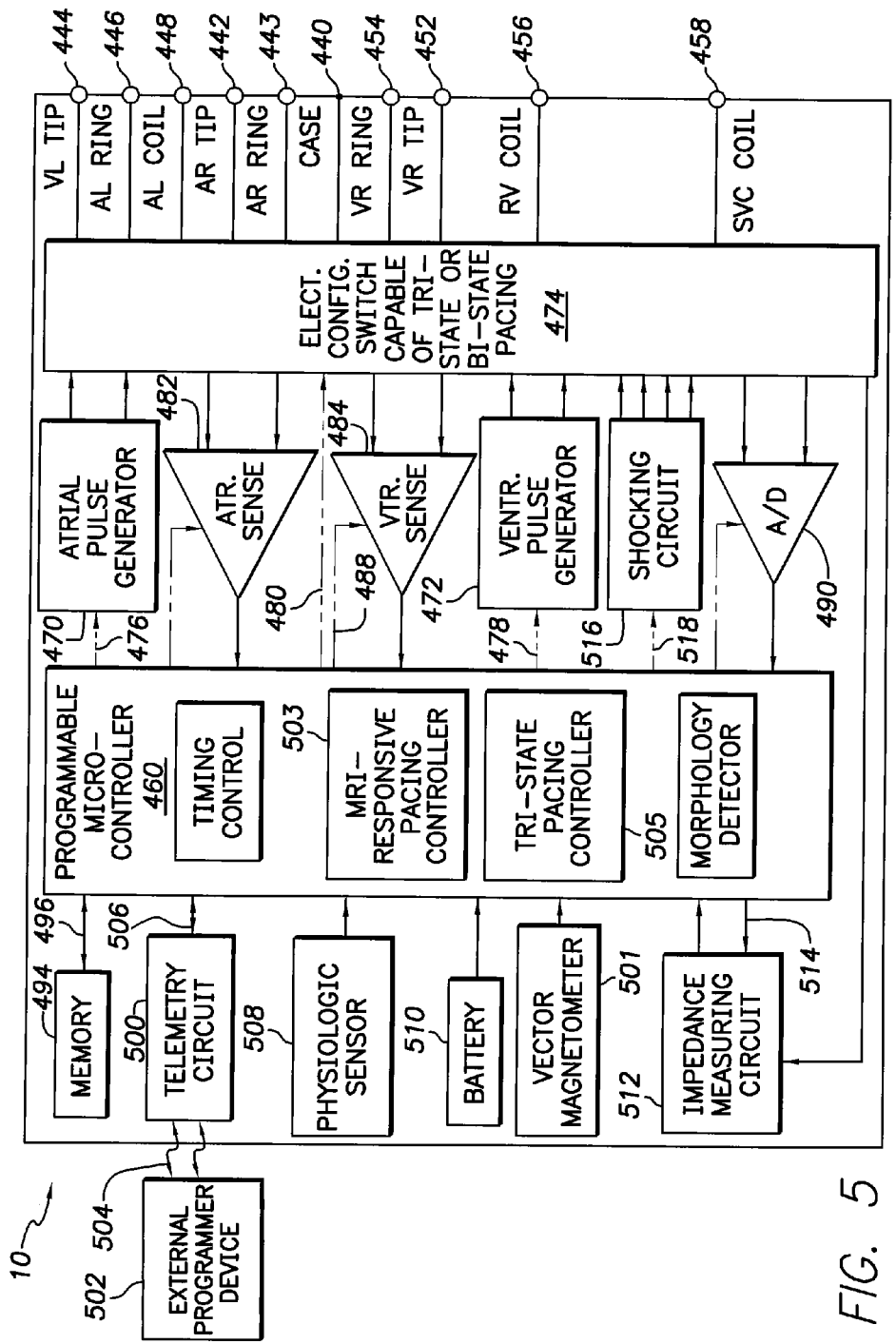
FIG. 5 is a functional block diagram of the pacer/ICD of FIG. 4, illustrating basic circuit elements that provide cardioversion, defibrillation and/or pacing stimulation in four chambers of the heart and particularly illustrating components for MRI-responsive pacing.

With reference to FIGS. 4 and 5, a description of the pacer/ICD of FIG. 1 will now be provided. FIG. 4 provides a simplified diagram of the pacer/ICD, which is a dual-chamber stimulation device capable of treating both fast and slow arrhythmias with stimulation therapy, including cardioversion, defibrillation, and pacing stimulation, as well as capable of detecting and responding to MRI fields.

To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 5. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 5, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial tip electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 5, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Switch 474 is configured to allow any output of the device to be selectively tri-stated, i.e. the switch includes internal components that allow outputs to be generated as normal bi-state outputs (positive vs. negative) or tri-sate outputs (positive, negative, open circuit.) This will be described in more detail below with reference to FIG. 6.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV Delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 5. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 5, pacer/ICD 10 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 512 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as MRI-responsive pacing is concerned, the device also includes a vector magnetometer 501 for detecting magnetic fields along three axes. Although shown as internal, the magnetometer may instead be an external component of the device. An MRI-response pacing control 503 receives signals from the magnetometer and responds to MRI fields using the techniques described above in connection with FIGS. 2-3. As already explained, in some cases, tri-state pacing is performed using an alternate pacing vector. Tri-state pacing is performed under the control of a tri-state pacing controller 505, which sends appropriate signals to switch 474 for tri-stating the outputs and for switching to an alternate pacing vector (i.e. an alternative pair of electrodes).

Figure 6:
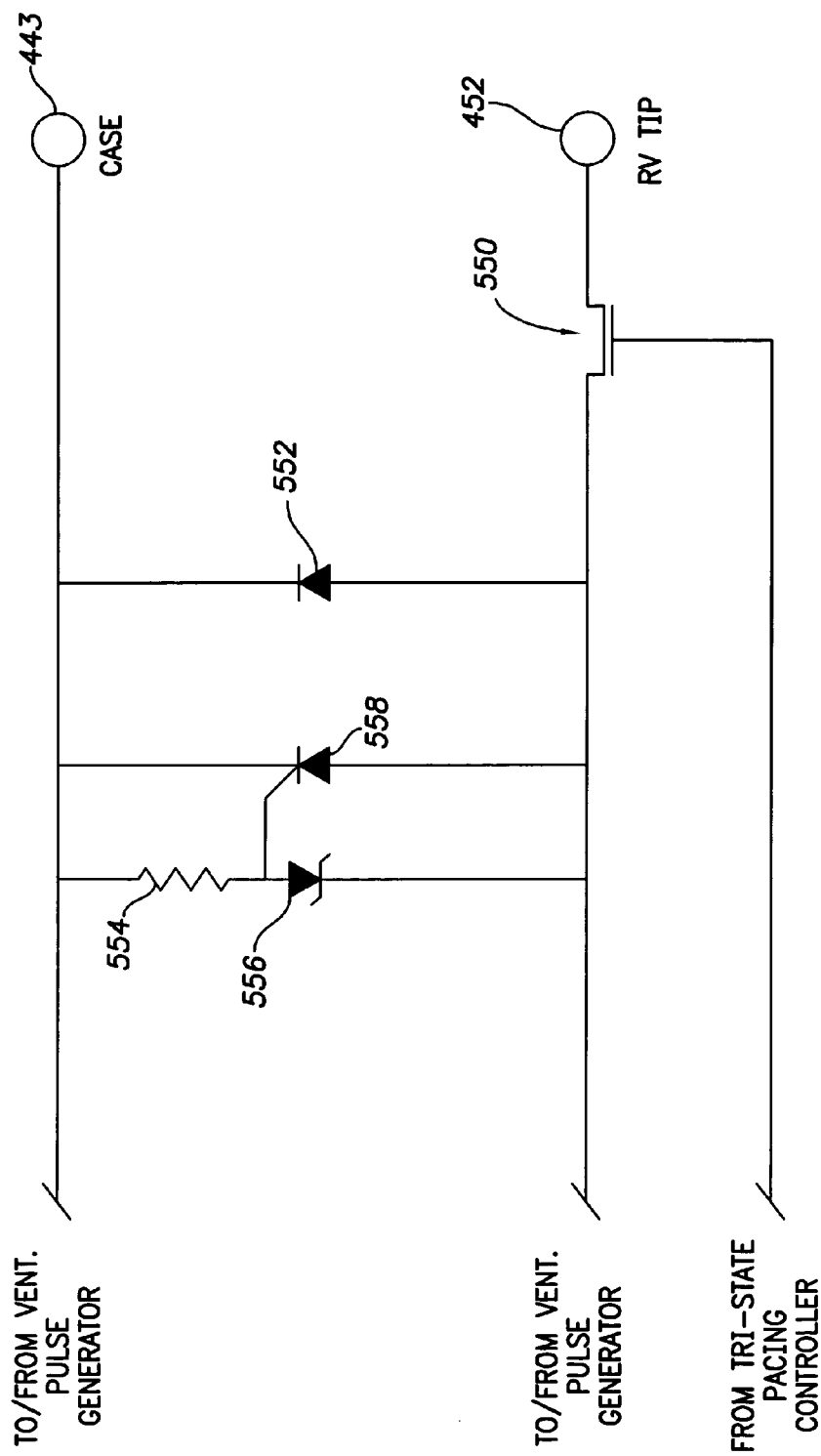
FIG. 6 provides circuit diagrams illustrating selected components a configuration switch of the pacer/ICD of FIG. 5 particularly illustrating components employed for tri-state pacing output.

FIG. 6 illustrates pertinent components of switch 474 for switching between bi-state and tri-state pacing outputs to the RV tip and case electrodes and for protecting against defibrillation shock damage. Similar circuit components are preferably provided in connection with other pairs of electrodes. The RV tip and case electrodes are merely illustrated as an example. Briefly, to generate a pacing pulse, the ventricular pulse generator (472 of FIG. 5) generates a voltage difference with a magnitude of typically 8 V between RV tip electrode 452 and device case electrode 443. For bi-state pacing, the high voltage field effect transistor 550 is kept closed, allowing the 8 volt difference to be applied between the case and the RV tip. During the tri-state pacing mode, the tri-state pacing controller (505 of FIG. 5) opens the transistor to block any current flow between the RV tip electrode and the ventricular pulse generator, thereby blocking any parasitic MRI currents from being conducted from the case electrode to the RV tip electrode through the device. The field effect transistor is preferably capable of withstanding 1000V. Note that if a pacing pulse needs to be delivered between the RV tip and case electrodes during application of strong MRI fields, the transistor is briefly closed to permit delivery of the pulse. Pacing pulses are typically less than 1 ms in duration and hence the transistor is only closed for a very short period of time.

Note that various circuit components are additionally provided to protect the pacing circuitry during delivery of defibrillation shocks while in the bi-state mode. More specifically, FIG. 6 illustrates a diode 552, a resistor 554, a Zener diode 556 and a silicon controlled rectifier (SCR) 558, coupled as shown. Diode 552 conducts any positive voltage greater than 0.7 volts. (Pacing pulses are always negative and hence are not blocked by diode 552.) The Zener diode-SCR circuit conducts when a negative voltage beyond 10 V is detected. That then triggers the SCR, which clamps down to 4 volts, thus preventing any voltage greater than 10 V from reaching the pulse generator circuitry. Hence, defibrillation shock voltages (generated initially between the RV coil of FIG. 4 and the device case) are blocked from damaging device pacing circuitry via internal circuit pathways interconnecting RV tip and case. However, these components provide possible paths for parasitic currents during an MRI, hence the need for the field effect transistor. Note also that during delivery of a defibrillation pulse (between RV coil and case), transistor 550 (which is coupled to the RV tip electrode) may be closed so as to provide an alternative means of protection of the internal circuitry.

What have been described are various systems and methods for MRI-responsive pacing using a pacer or ICD. Principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. In an implantable medical device, a method comprising:
   operating in a first pacing mode to deliver pacing therapy using a first set of device outputs and a first pacing vector defined by a first pair of electrodes; detecting magnetic fields;
   detecting for static component of the magnetic fields and if any are detected, determining a value representative of the strength of the static component and comparing the static component value to a static magnetic field threshold;
   detecting for pulsed gradient components of the magnetic fields and if any are detected, determining a value representative of the strength of the pulsed gradient components and comparing the pulsed gradient component value to a pulsed gradient threshold; and
   controlling device functions differently based on whether both the static component value and the pulse gradient component value exceed their respective threshold, only one of the static component value and the pulse gradient component value exceed their respective threshold, and neither of the static component value and the pulse gradient component value exceed their respective threshold.

2. The method of claim 1 wherein the value representative of a strength of the pulsed gradient components is the mean of |dB/dt|.

3. The method of claim 1 wherein detecting for pulsed gradient components of the magnetic fields comprises measuring a value representative of a strength of the pulsed gradient components along a predetermined axis.

4. The method of claim 3 wherein the value representative of a strength of the pulsed gradient components along a predetermined axis is the mean of $|dB_i/dt|$ where "i" represents the predetermined axis.

5. The method of claim 1 wherein the pacing mode is any mode other than fixed rate ventricular pacing (VOO) and the first set of device outputs are bi-state pacing outputs and when both the static component value and the pulse gradient component value exceed their respective threshold, further comprising switching the pacing made to VOO and the device outputs to tri-state pacing outputs.

6. The method of claim 5 further comprising switching the pacing vector to a second vector defined by a second pair of electrodes different from the first pair of electrodes.

7. The method of claim 6 wherein the first pair of electrodes are RV tip and an RV ring electrodes and wherein the second pair of electrodes are RV tip and device housing electrodes.

8. The method of claim 1 wherein the pacing mode is any mode other than fixed rate ventricular pacing (VOO) and the first set of device outputs are bi-state pacing outputs and when only the static component value exceeds its threshold, further comprising switching the device outputs to tri-state outputs.

9. The method of claim 8 further comprising switching the pacing vector to a second vector defined by a second pair of electrodes different from the first pair of electrodes.

10. The method of claim 8 further comprising maintaining the pacing mode.

11. The method of claim 1 wherein the pacing mode is any mode other than fixed rate ventricular pacing (VOO) and the first set of device outputs are bi-state pacing outputs and when only the pulse gradient component value exceeds its threshold, further comprising switching the pacing mode.

12. The method of claim 11 further comprising maintaining the device outputs as bi-state pacing outputs.

13. The method of claim 1 wherein the pacing mode is any mode other than fixed rate ventricular pacing (VOO) and the first set of device outputs are bi-state pacing outputs and when neither of the static component value and the pulse gradient component value exceed their respective threshold, further comprising maintaining the pacing mode and the bi-state pacing outputs.

14. An implantable medical device comprising:

means for operating in a first pacing mode to deliver pacing therapy using a first set of device outputs and a first pacing vector defined by a first pair of electrodes means for detecting magnetic fields;

means for detecting for static component of the magnetic fields and if any are detected, determining a value representative of the strength of the static component and comparing the static component value to a static magnetic field threshold;

means for detecting for pulsed gradient components of the magnetic fields and if any are detected, determining a value representative of the strength of the pulsed gradient components and comparing the pulsed gradient component value to a pulsed gradient threshold; and means for controlling device functions differently based on whether both the static component value and the pulse gradient component value exceed their respective threshold, only one of the static component value and the pulse gradient component value exceed their respective threshold, and neither of the static component value and the pulse gradient component value exceed their respective threshold.

15. In an implantable cardiac stimulation device having a voltage generator for applying a voltage across a first electrode and a second electrode for pacing the heart of a patient, a method comprising:

detecting magnetic fields associated with magnetic resonance imaging (MRI);

detecting a strength of pulsed gradient components of the magnetic fields; and if the strength of the pulsed gradient components of the magnetic field is above a predetermined parasitic current risk threshold level, establishing current paths between the voltage generator and first and second electrodes only during pace pulse delivery, otherwise opening the current path between the voltage generator and one of the first and second electrodes.

* * * * *